United States Patent [19]

Turner

[11] Patent Number: 4,812,412

[45] Date of Patent: Mar. 14, 1989

[54] STANDARD SPECIMEN AND METHOD OF MAKING AND USING SAME

[75] Inventor: James N. Turner, Delmar, N.Y.

[73] Assignee: Health Research Inc., Albany, N.Y.

[21] Appl. No.: 19,063

[22] Filed: Feb. 26, 1987

[51] Int. Cl.⁴ ............................................. G01N 31/00
[52] U.S. Cl. ............................................ 436/15; 436/8
[58] Field of Search ................................ 436/8–19, 436/86, 87, 88, 63, 174; 424/3; 252/408.1; 422/61, 55; 427/2; 428/67

[56] References Cited

U.S. PATENT DOCUMENTS

| | | | |
|---|---|---|---|
| 3,679,450 | 7/1972 | Beightol | 117/3 |
| 4,020,005 | 4/1977 | Lang | 436/19 |
| 4,029,419 | 6/1977 | Schumann | 356/173 |
| 4,053,433 | 10/1977 | Lee | 252/408.1 |
| 4,225,669 | 9/1980 | Melnick | 435/29 |
| 4,238,384 | 12/1980 | Blumberg et al. | 252/408.1 |
| 4,353,856 | 10/1982 | Mück et al. | 424/3 |
| 4,390,452 | 6/1983 | Stevens | 252/408.1 |
| 4,431,766 | 2/1984 | Christie et al. | 252/408.1 |
| 4,434,234 | 2/1984 | Adams et al. | 436/63 |
| 4,505,233 | 3/1985 | Saito et al. | 252/408.1 |
| 4,510,169 | 4/1985 | Linner | 424/3 |
| 4,523,852 | 6/1985 | Bauer | 356/421 |
| 4,544,546 | 10/1985 | Wang et al. | 424/3 |
| 4,575,452 | 3/1986 | Lee et al. | 436/86 |

Primary Examiner—Barry S. Richman
Assistant Examiner—T. J. Wallen
Attorney, Agent, or Firm—Curtis, Morris & Safford

[57] ABSTRACT

This invention provides a standard specimen useful for the quantitative evaluation of performance of stains, staining solutions and staining processes used on biological specimens, and also for the evaluation of dyestuffs. The standard specimens are comprised of extracts of biological materials containing protein and/or nucleic acid which are incorporated into a reproducible plastic matrix of controlled thickness. The standard specimen so produced is useful in the quantitative performance evaluation of a dyeing or staining process, thereby providing information for process control and quantitative analysis and comparisons. The invention also provides for the method of preparing the standard specimen of the invention, as well as for the method of using the standard specimen.

21 Claims, 9 Drawing Sheets

STANDARD SPECIMEN AND METHOD OF MAKING AND USING SAME

FIELD OF THE INVENTION

The field of the invention is a standard specimen, and in a more particular vein, a standard specimen useful for the quantitative evaluation of the performance of stains, staining solutions and processes used on biological substrates. This includes for example, biological specimens such as hematological, histological or cytological specimens. It is also useful for the quantitative evaluation of dyeing and stain solutions. The standard specimens may be used, for example, to provide a baseline for the comparison of inter and intra laboratory procedures, specimens processed under different staining conditions and at different times and specimens which have different physiologic or pathophysiologic states. The standard specimens provide a correlation between chemical and optical characteristics of stain performance and dyes and dye solutions.

BACKGROUND OF THE INVENTION

Quantitative analysis, particularly the automated quantitative analysis of cytological, hematological and histological specimens requires exacting control of dyes, dye solutions and staining processes. Quantitative measurements used to differentiate normal from pathologic specimens may be expressed either as light transmission, integrated optical densities, ploidy, light scattering, light polarization effects and fluorescence. Since these measurements are strongly dependent on the staining process, a characterization and standardization of the dyes and staining solutions used is necessary. The conventional methods of standardizing and evaluating dyes and staining solutions include the physical and chemical characterization of the dyes and also the direct visual assessment of stain performance.

However, the physical-chemical approach of quantitating the dye and its concentration does not provide any information on the specimen-dye interactions and cannot measure changes in the process, as the dyeing or staining baths which are used are exposed to different conditions.

The visual assessment of stain performance suffers from the lack of a reproducible specimen by which the performance can be quantitatively evaluated. Non-standardized specimens can only provide a qualitative analysis of the process and lack the necessary reproducibility to provide a quantitative analysis.

The difficulty of comparing biological samples quantitatively is due in large part to variations in the staining process. Dyes vary from batch to batch, and their solutions may vary over time for the same batch or even for the same preparation. This variability is especially true for natural dyes; and the Papanicolaou stain, although very useful for cytology, is difficult to standardize. This shortcoming is particularly problematic for automated analysis.

Even such promising digital parameters as cytoplasmic staining intensity, ploidy and nuclear integrated optical density, are strongly influenced by variations in the staining process. Cytology smears can vary by as much as 10–23%, mostly due to specimen processing and staining. A better understanding and control of dyes and staining processes is needed before automated methods of cytologic screening can be widely applied.

Therefore a need exists for a standard specimen which is reproducible to high degree of precision. Each sample must react in the same way with the staining solution and must stain uniformly so that light transmission does not vary for different microspectrophotometric fields.

Specimens having slight variations in the concentration of biological molecules which bind the dyes, or having any variation in thickness, do not meet the necessary criteria, since the transmitted light varies in accordance with the amount of dye bound along the light path. For these reasons, naturally occurring biological objects, even the most carefully controlled cell cultures, cannot therefore be used.

A standard specimen, to be useful, must be composed of molecules similar to those which bind dyes in the biological objects of interest, but must be strictly controlled so that a number of samples subjected to the same staining solutions at the same time will produce equivalent microspectrophotometric measurements to a high degree of precision. This must be true for different fields in the same specimen and different specimens.

The instant invention meets these needs, providing a standard specimen which can calibrate stain uptake and define a quantitative baseline for sample comparison. The inventive specimen utilizes extracts of biological preparations containing proteins and/or nucleic acids, which mimic the staining characteristics of biological specimens. These extracts are incorporated into a reproducible matrix which can be sectioned to a controlled thickness. This ensures the production of a large number of samples with almost identical capability for dye binding.

One of the advantages obtained by using the standard specimen according to the invention is that the standard specimen can quantitate the stain performance of stains, staining solutions, and staining processes used on biological substrates and can calibrate the process, under any conditions, regardless of the dye used or its concentration or the conditions to which it is exposed. The standard specimen will thus allow detailed quantitation and evaluation of the dyeing or staining process, thereby providing information for process control and quantitative analysis comparisons.

OBJECTS OF THE INVENTION

It is an object of the invention to provide a standard specimen which can quantitate performance evaluation of staining processes used on biological substrates and evaluate dyeing processes.

It is a further object of this invention to provide a standard specimen which can calibrate the process under any conditions, regardless of the dye used, its concentration, or the conditions to which it is exposed.

It is an additional object of the invention to provide a standard specimen which will allow for detailed quantitation of the dyeing or staining process, thereby providing information for process control and quantitative analysis and comparisons.

It is another object of this invention to provide a method of making a standard specimen which can quantitate performance evaluation of staining processes and dyeing processes and which can calibrate the process under any conditions regardless of the dye used, its concentration or the conditions to which it is exposed.

It is an additional object of this invention to provide a process for making a standard specimen which will allow for detailed quantitation of the performance of the dyeing or staining process, thereby providing information for process control and quantitative analysis and comparisons.

It is yet another object of this invention to provide a process for using the standard specimen which is made by the method of the invention, and method of use of which is characterized by the aforementioned advantages.

These and other objects are met by the present invention.

STATEMENT AND ADVANTAGES OF THE INVENTION

In one of the aspects, the invention is directed to a standard specimen which is manufactured by the method of incorporating an extract of a biological material containing protein and/or nucleic acid into a reproducible plastic matrix of controlled thickness. Biological materials which may be used are, for example, bovine liver acetone powder, nucleoprotamine, and defatted horse muscle. The plastic matrix can be an epoxy, for example glycol methacrylate epoxy. The controlled thickness is obtained by slicing a block of the standard specimen material on a microtome.

In another aspect, the present invention is directed to a method of making a standard specimen for the quantitative performance evaluation of staining processes used on biological substrates, such as, histological, hematological and cytological specimens, and dyeing or staining solutions. The standard specimens are comprised of extracts of biological materials containing protein and/or nucleic acid. Some biological materials which may be used, for example, are bovine liver acetone powder, nucleoprotamine, and defatted horse muscle. The extracts are incorporated into a reproducible plastic matrix of controlled thickness. The plastic matrix can be an epoxy, such as glycol methacrylate epoxy. The controlled thickness of the standard specimen is then obtained by slicing a block of the standard specimen material on a microtome.

In an additional aspect, the invention is directed to a method of using the standard specimen for the quantitative performance evaluation of staining processes used on biological substrates, such as, histological, hematological and cytological specimens, and dyeing or staining solutions.

Numerous advantages accrue with the practice of the present invention. To calibrate stain performance, a standard specimen must have a spectral response similar to that of the object or objects being stained. For example, in the case of cervicovaginal cytology the spectral information varies from deep blue (nuclei) to blue-green (intermediate cell cytoplasm) to red (superficial cell cytoplasm). The inventive standard specimens give a spectral response across the full range of spectra recorded from Papanicolaou-stained cervicovaginal smears. Thus stain performance on all cellular details can be optimally evaluated and calibrated.

The standard specimen prepared in accordance with the invention can therefore calibrate stain uptake and be used to define a quantitative baseline for sample comparison. It can quantitate stain performance and be used to calibrate the process under any conditions, regardless of the dye used, its concentration, or the conditions to which it is exposed.

The standard specimen allows for detailed quantitation of the dyeing or staining process, thereby providing information for process control and quantitative analysis and comparisons. A large number of specimens can be produced which are reproducible to a high degree of precision. Also, each replicate reacts in the same way with various staining solutions.

Moreover, each sample stains uniformly, with minimal variation in light transmission between samples and between microspectrophotometric fields in the same sample. In accordance with the invention, light transmission at specific wavelengths is measured using a microspectrophotometer attached to a light microscope. Variation in light transmission across the central portion of individual samples is found to be about ±5%. Variation between samples cut from the same plastic block and stained at the same time is also only about ±5%.

Clinical samples (cytology smears) stained at different times can show variations of from about 15 to 23% mostly due to specimen processing and staining. Therefore, the variation in the standard specimen is substantially less than batch to batch variations in clinical samples.

The standard specimen of the instant invention is therefore useful in the evaluation of various biological specimens for testing purposes, for example, in the automated analysis of cytological, hematological, and histological specimens. It is also useful in the evaluation of the activity of dyestuffs and/or pigments in the dyestuff and textile industry.

In the following section the invention is described in greater detail to illustrate several of its embodiments.

DESCRIPTION OF CERTAIN PREFERRED EMBODIMENTS

A central feature of the present invention is the incorporation of extracts of biological objects into a reproducible matrix. The extract-containing matrix can then be sectioned. The extracts which may be used, for example, are bovine liver acetone powder, nucleoprotamine, and defatted horse muscle. Other extracts may be used. The concentration of biological molecules which bind the dyes, the physical and chemical parameters of the preparations, such as pH, ionic strength, temperature, fixation, dehydration and embedding, along with specimen thickness, are carefully controlled. However, it is the recognition that certain extracts which contain proteins or nucleic acids, or both, from biological objects, may be reproducibly incorporated into a sample of controlled thickness, which sample can then be stained by exposure to dye solutions, which is central to the instant invention.

The extracts are resuspended in appropriate solvents, for example, water, salt solutions, or organic liquids. Those resuspended in aqueous solvents are processed through transition solvents to make them miscible with the matrix material.

In one embodiment, bovine liver powder is resuspended in water by stirring for six hours to several days. Sodium azide is added in low concentration to prevent bacterial growth. The mixture is spun in a bench top centrifuge at low speed and the pellet discarded. The supernatant is spun at high speed to form a pellet composed of the smaller particles. The supernatant is decanted and the pellet fixed in either neutral buffered formalin, or an appropriate concentration of alcohol. A minimum period of about 48 hours is used to insure thorough penetration of the fixative. The sample is then dehydrated through graded ethanols and then embedded in a plastic matrix, for example, a glycol methacrylate epoxy. The controlled thickness of the specimen is then obtained by slicing a block of the specimen material on a microtome. When the microtome is carefully set and the mechanical settings are unchanged, the light transmission through the plastic portion of the section—not the sample portion—varies for different sections processed at the same time by approximately ±2%. This indicates that the section thickness also varies by only ±2%. After sectioning, the samples are then mounted on glass slides, stained, and a cover slip attached with mounting media. Specimens may be processed by using any appropriate stain, such as the Papanicolaou stain.

In accordance with the invention, light transmission at specific wavelengths is measured using a microspectrophotometer attached to a light microscope. Variation in light transmission across the central portion of individual samples is found to be about ±5%. Variation between samples cut from the same plastic block and stained at the same time is also only about ±5%.

Clinical samples stained at different times show variations of from about 15 to 23%; therefore the variation in the standard specimen is substantially less than batch to batch variations in clinical samples.

Extinction curves have also been measured for the samples and they are consistent with the spectra of the staining solutions, and the composition of the specimens.

In another embodiment nucleoprotamine samples from salmon testes are prepared and measured by the same methods, as above, except that the solvent is varied before the pellet was formed. Nucleoprotamine may be resuspended in water, and in 10% NaCl. The water suspensions are processed in the same way as the liver powder. Nucleoprotamine also may be resuspended in 10% NaCl at pH 8.0, and some samples may be pH shifted by adding small amounts of 0.5N HCl or NaOH to the suspension before the second spin. These changes produce specimens with different spectra having very different blue to red extinction ratios. The spectra of the nucleoprotamine samples can be readily controlled. This is of significance since different cell types have spectra which vary in this way.

In yet a further embodiment, defatted horse muscle represents a type of preparation for which the extract goes into solution, opposed to suspension. This extract is dissolved directly into one of the epoxy components, mixed with the other components, cured, sectioned, and stained as above.

Further objects of the invention, together with additional features contributing thereto and accruing therewith, will be apparent from the following examples of the invention.

EXAMPLE I

A crude isolation of nucleoprotamine from salmon testes is resuspended (10 mg/ml.) in distilled water or 10% NaCl at pH 8.0. A clean-up spin is followed by a spin at 1,600 g for one hour. Samples dissolved in NaCl are pH shifted by adding 50 to 100 ul of 0.5N. HCl or NaOH to 6 ml of sample. The pellets are fixed in buffered formalin or 95% ethanol for 48 hours, embedded in JB-4 histoplastic, and sectioned at 4,6 and 8 microns, and Papanicolaou stained.

Transmitted light intensities are measured using a Zeiss microspectrophotometer. Extinction curves show a sharp peak centered at 530 nm. and a broad peak centered between 620 and 640 nm., the ratio of which varies depending on the preparation conditions. The uniformity of the samples varies with preparation conditions, the most uniform being those dissolved in distilled water or 10% NaCl to which 50 to 100 ul of 0.5N. HCl or NaOH are added. The light transmission (530 and 620 nm.) of the plastic section surrounding the specimen varies by at most 1.7%, indicating that the section thickness is reproducible. Similar measurements of eight sections from the same sample stained together show a variation of 8% to 11%, depending on the image magnification at the entrance aperture to the photometer. Measurements of individual samples shows 4 to 5% maximum variation. The 6 micron thickness is the most uniform and produces the most consistent results.

EXAMPLE II

Bovine liver powder is resuspended in distilled water (3 mg/ml.) by stirring for six hours to several days. Sodium azide is added in low concentration to prevent bacterial growth. The mixture is spun in a bench top centrifuge for a start clean up at low speed and the pellet discarded. The supernatant is spun for 1 hour at 1,600 g to form a pellet composed of the smaller particles. The supernatant is decanted and the pellet fixed in 10% neutral-buffered formalin for a minimum period of 48 hours. The sample is then dehydrated through graded ethanols, embedded in JB-4 Histoplastic, and sectioned at 6 and 8 microns on a Sorvall JB-4 Histotome with glass knives, and Papanicolaou stained.

Transmitted light intensities are measured using a Zeiss microspectrophotometer. Extinction curves show distinct green and red peaks at about 530 and 640 nm, respectively, with a ratio of $E_{530}/E_{640}=2.1$. Variation in light transmission across the central portion of individual samples is found to be about ±5%. Variation between samples cut from the same plastic block and stained at the same time is also only about ±5%.

BRIEF DESCRIPTION OF THE DRAWINGS

General:

Materials and methods used are as follows:

A. Staining Solutions:

A modified Papanicolaou stain was applied with a Shandon Varistain 24-3 automatic staining machine. Gill I hematoxylin and eosin EA-65 were from Surgipath Medical Industries. The Orange G consisted of 0.2% Orange G and 0.015% phosphotungstic acid in 95% ethanol with 2.3 ml of glacial acetic acid per 1000 ml of solution.

B. Spectrophotometry Of Staining Solutions:

A Perkin-Elmer 320 spectrophotometer was used to measure the extinction curves of the staining solutions. The staining solutions were measured undiluted using cuvettes with a 0.3 mm path length.

C. Sample Production

Crude extracts of nuclooprotamine from salmon testes and bovine acetone liver powder (available from the Sigma Chemical Company) were used as specimens. Nucleoprotamine was suspended (10 mg/ml) in either distilled water or 10% NaCl at pH 8.0. After a short clean-up centrifugation the pH of some suspensions was shifted to 5.3 or 10.9 by adding HCl or NaOH. The suspension to which no acid or base was added had an equilibrium pH of 7.3. Each suspension was centrifuged at 1,600 g for 1 h, and the pellet was fixed in either 95% ethanol or 10% neutral-buffered formalin for a minimum of 48 h. The pellets were embedded in JB-4 histoplastic.

The liver powder was suspended in distilled water (3 mg/ml). The suspension was spun first for a short clean up then for 1 h at 1,600 g. The pellets were fixed in 10% neutral-buffered formalin for a minimum of 48 h and embedded in JB-4 histoplastic.

The embedded specimens were sectioned on a Sorvall JB-4 Histotome at 6-μm and 8-μm thickness with glass knives.

D. Microspectrophotometry:

A Zeiss microspectrophotometer attached to a Zeiss photomicroscope was used to measure light intensity as a function of wave length. The entrance aperture of the photometer was always the same and depending on the objective lens used corresponded to either 0.20 or 0.48 mm diameter field at the specimen. The stability and sensitivity of the photometer were such that light intensity was measured to ±0.5%. The color wedge used as a filter, combined with the size of the field aperture, produced a distribution of wavelengths equal to 10 nm across each field of measurement.

Figure 1:
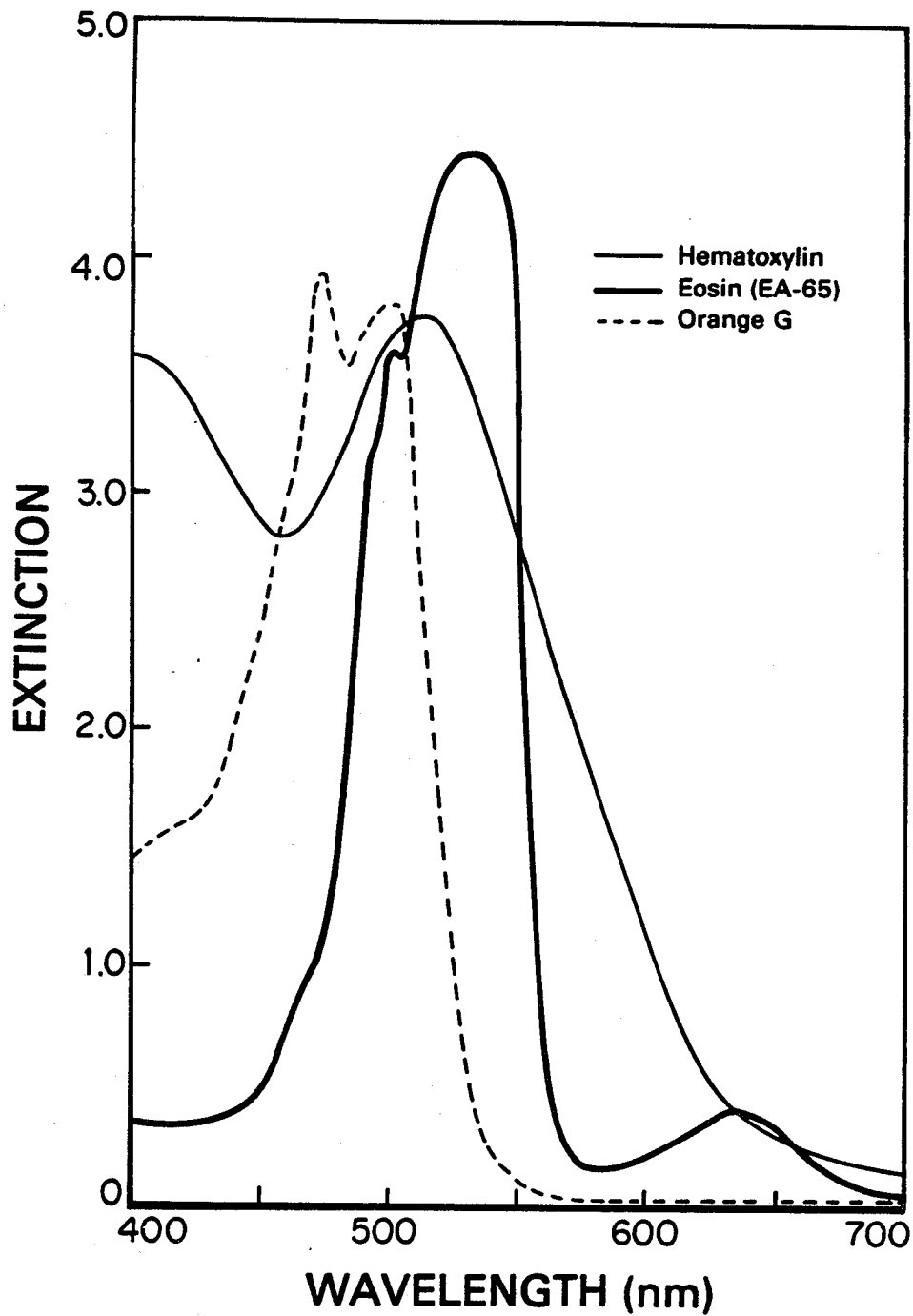

FIG. 1: consists of extinction curves for the staining solutions. The hematoxylin curve has an expected peak at about 520 nm. The peak at 400 nm. is higher than expected but the difference is attributed to the particular formulation (Gil) and is repeatable. The eosin (EA-65) curve has the typical shape with peaks at 530 and 630 nm., reflecting eosin Y and the light-green component of the staining solution respectively. The Orange G extinction curve has an expected peak at 500 nm. and a strong cutoff above 570 nm. This curve has an additional peak at 472 nm. repeatable for the formulation.

A triple crossover for all three staining solution occurs at approximately 506 nm. (range, 504 to 508 nm.) Eosin and hematoxylin have second crossover at 550 nm., consistent with reported value of about 570 nm. Two other crossovers are observed at 634 and 656 nm. Orange G and hematoxylin cross over at 456 and 506 nm.

Figure 2:
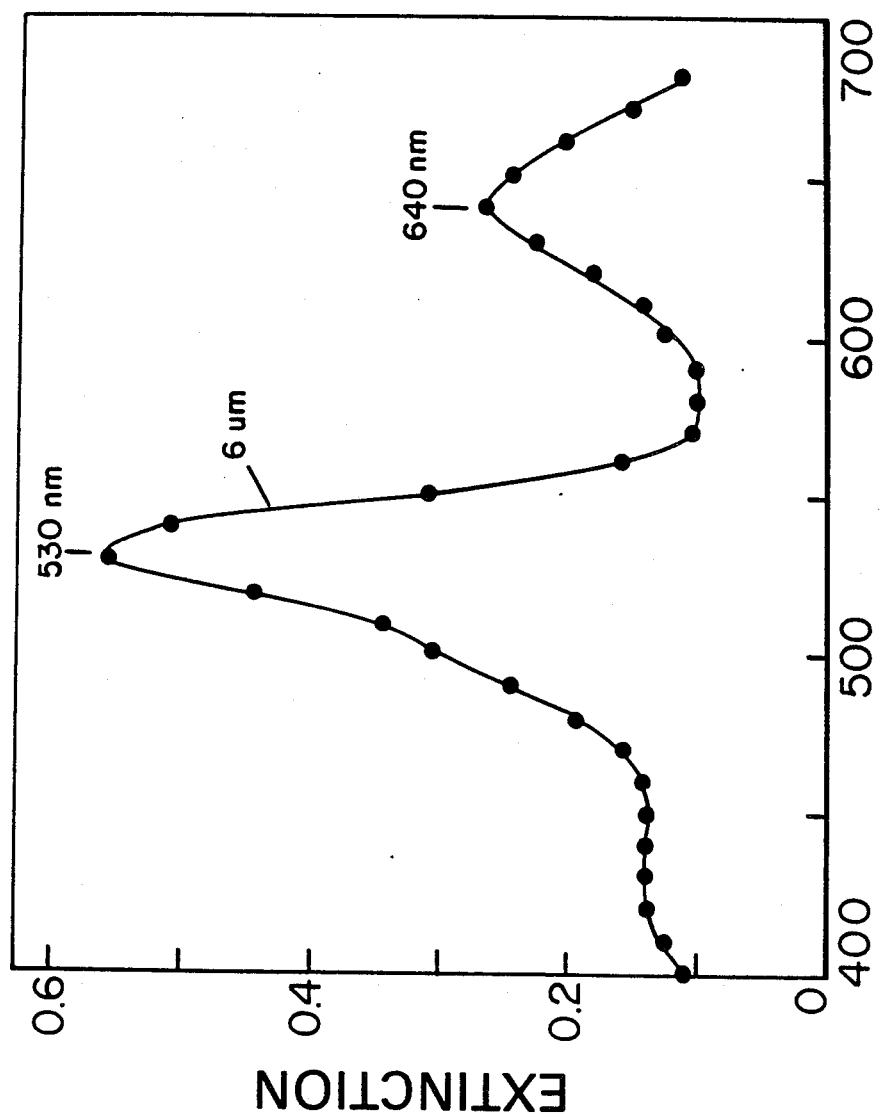

FIG. 2: depicts the extinction curve for a standard specimen of bovine liver acetone powder. Distinct green and red peaks are observed at about 530 and 640 nm. respectively, with a ratio $E_{530}/E_{640}=2.1$. A tungsten halogen light source makes the sample appear blue with a red highlight when viewed through a microscope.

Figure 3:
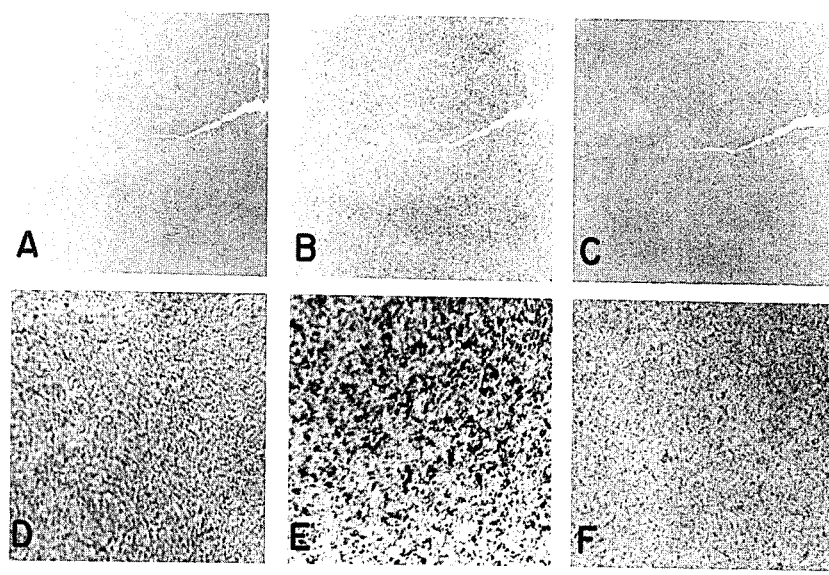

FIG. 3: consists of photomicrographs of a liver powder standard specimen. Low magnification images (A–C) show the uniformity of the specimen as viewed with no filter or with interference filters having 10-nm. band pass as filtered at 540 and 640 nm. The unfiltered image shows some structure, which has a consistent size and texture across the specimen. The contrast of these features is enhanced by a 540-nm. interference filter, whereas the image appears essentially featureless when viewed through a 640-nm. interference filter. The higher-magnification images (D–F) represent approximately the image area passed by the photometer aperture, corresponding to a field size of 0.2 mm. at the specimen. The transmitted light intensity of fields accross the specimen was uniformly within ±5%. (No measurements were taken within one field diameter of the specimen edge.) Thus the texture observed at 540 nm. did not significantly affect the uniformity of the transmitted light for this field size.

Figure 4:
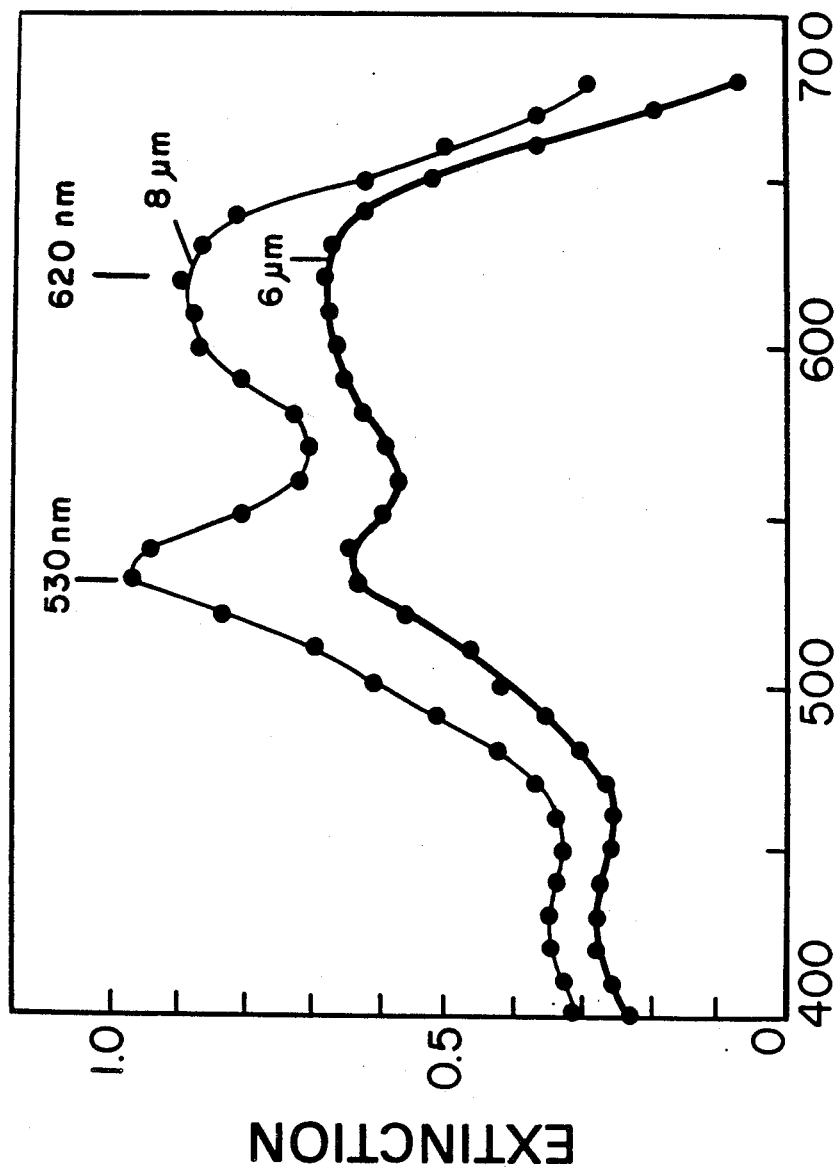

FIG. 4: Two extinction curves for nucleoprotamine resuspended in water. The curves are for specimens from the same block cut at different thicknesses. The thicker specimen, as expected, shows greater extinction over the entire range of wavelengths. Characteristic green and red peaks occur at 530 and 620 nm; the 530-nm peak is more sharply defined. $E_{530}/E_{620}=0.94$ for the 6-μm thickness and 1.1 for the 8-μm thickness. This specimen appears deep blue when viewed through the microscope.

Figure 5:
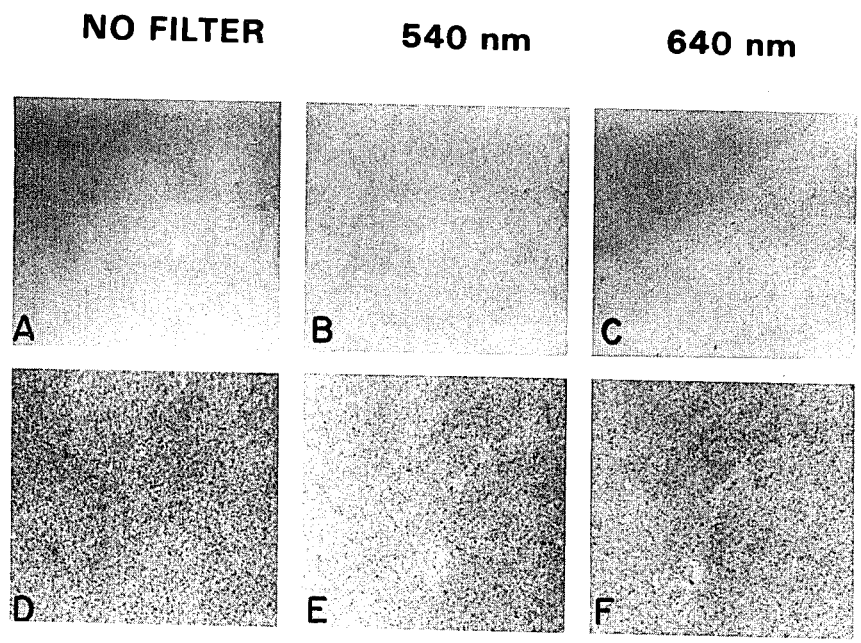

FIG. 5: Photomicrographs of the preparation measured in FIG. 4. These specimens appear featureless at the lower magnification (A–C). The higher magnification (D–F) shows some fine structure in the unfiltered image and, with reduced contrast, in the filtered images. The transmitted light intensities of randomly selected fields across the specimen were uniform within ±5%, except within one field diameter from the edge.

Figure 6:
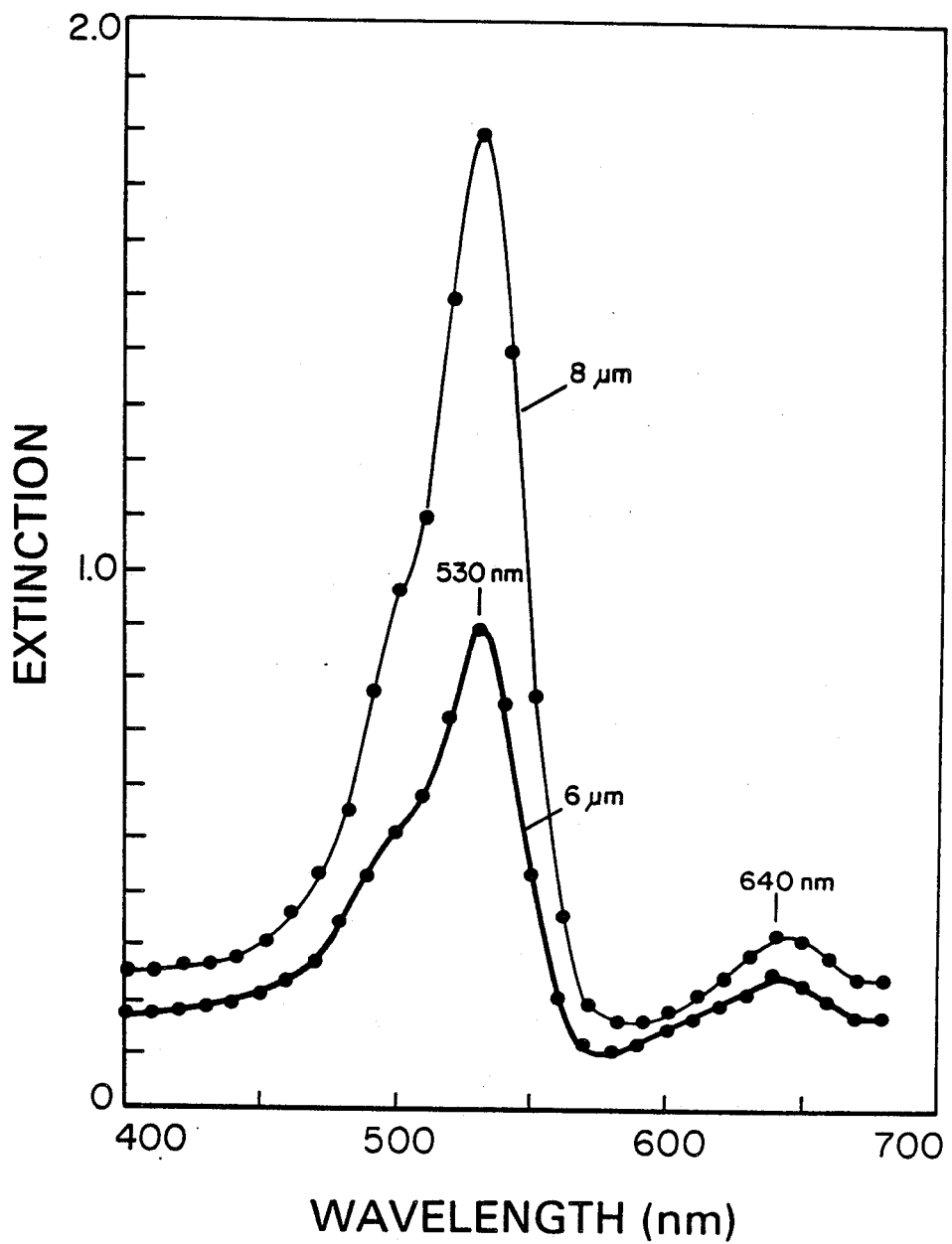

FIG. 6: Extinction curves for nucleoprotamine resuspended in 10% NaCl at pH 8.0 for which the pH was shifted to 10.9 before the pelleting centrifugation. The thicker specimen shows greater extinction at all wavelengths. Characteristic green and red peaks occur at 530 nm and 640 nm respectively. The 530-nm peak height is twice as large as the corresponding peak at the unshifted pH (FIG. 4,) and has a shoulder on the blue side. The red peak is centered at 640 nm rather than 620 nm, and the peak height is about one-third that of the corresponding peak at the unshifted pH (FIG. 4). $E_{530}E_{640}$ 3.6 and 5.5, for the 6-μm and 8-μm thickness respectively. This preparation appears reddish-brown when viewed through the microscope, due to the high extinction in the blue-green region and the low extinction in the red.

Figure 7:
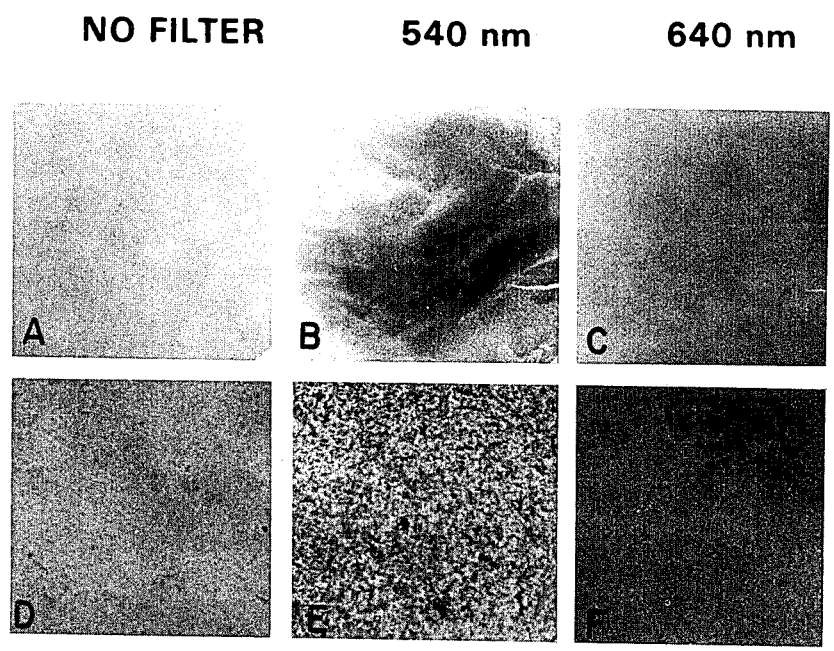

FIG. 7: Photomicrographs of the FIG. 6 specimen, photographed unfiltered and through the 540- and 640 nm. interference filters. It has more structural features than the other specimens and is the only one showing significant features at lower magnifiction. However, the relative contrast of these areas is enhanced by the photographic procedures, and the images recorded through the 640-nm filter show no structure. The transmitted light was uniform within ±5%. The nucleoprotamine resuspension is most efficient in 10% NaCl at pH 8.0, which is its condition of maximum solubility.

Figure 8:
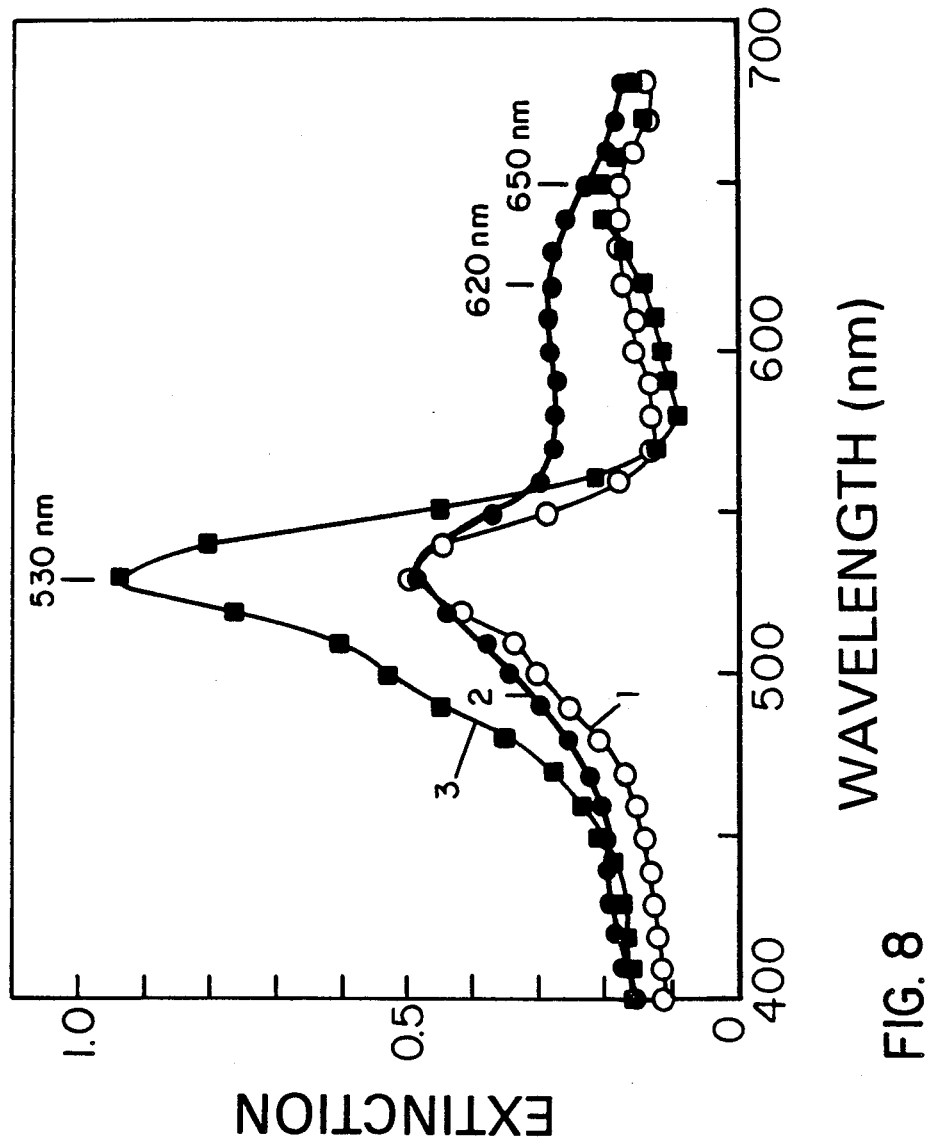

FIG. 8: Shows the effects of shifting the pH before pelleting. The extinction curves are quite different for the shifts studied. The green peak is always centered at 530 nm but is twice as large at pH 10.9 as at pH 7.3 (no acid or base added) or pH 5.3. The latter two specimens have the same maximum value and relatively small differences in shape on the blue side of the peak. The red region, in contrast, is essentially the same at pH 10.9 and 7.3 but is different at pH 5.3, where a plateau occurs to about 630 nm followed by a slow decline for longer wavelengths. Curve 3 of FIG. 8 and the 6-μm curve of FIG. 6 are measurements of different specimens prepared in he same way. Comparison of the two curves shows excellent reproducibility.

Figure 9:
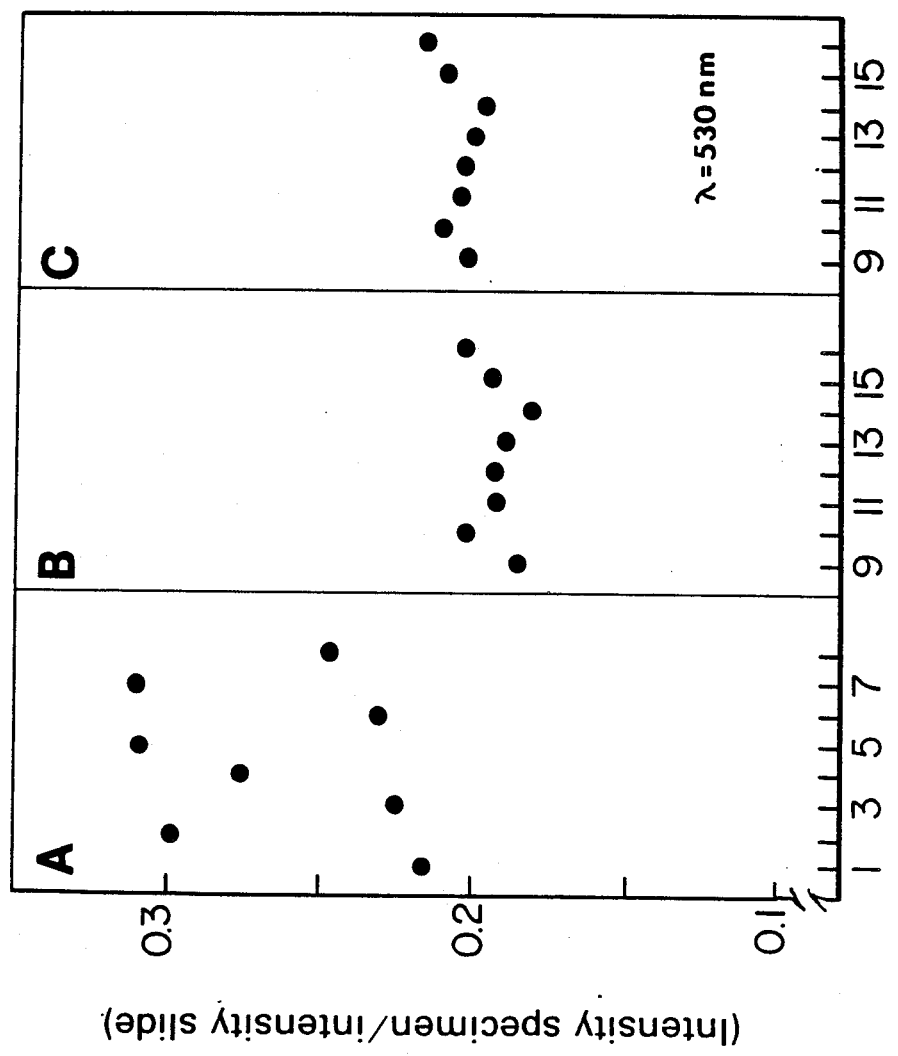

FIG. 9: Shows the effects of variations in specimen thickness. Sixteen specimens from the same block of nucleoprotamine resuspended in water were processed at the same time through the same staining solutions. The first eight sections were obtained by the usual procedure and showed a variation of transmitted light (specimen intensity divided by slide intensity) of ±15% at 540 nm (FIG. 9A). The second eight were sectioned by the same procedure, but special attention was given to the mechanical stability of the microtome, especially the clamping of all component parts. These precautions limited the variation of transmitted light to ±5.5%

(FIG. 9B). The plastic section surrounding the specimen region showed a variation of ±3.3% in FIG. 9A and ±0.85% in FIG. 9B, confirming that the uniformity of specimen thickness is clearly improved by special care in performing the microtomy. Finally the effect of the sampled field size was investigated. The area of the field passed by the photometer entrance aperture was increased nearly five times for the experiments in FIG. 9C, compared to FIG. 9B. For the larger field the variation of transmitted intensity was ±4.5% for the specimen and ±1.3% for the plastic section, a difference of only 2% and 1.% respectively from the smaller field. Thus the smaller field size was adequate. The terms and expressions which have been employed are used as terms of description and not of limitation, and there is no intention in the use of such terms and expressions of excluding any equivalents of the features shown and described or portions thereof, it being recognized that various modifications are possible within the scope of the invention.

What is claimed is:

1. A standard specimen for the quantitative evaluation of stain performance in staining processes which utilize dyes to stain cells or tissues which stained cells or tissue exhibit characteristic spectra when subjected to light transmission analysis, which standard specimen comprises a uniform amount of biological material extracted from cells or tissue incorporated into a plastic matrix which specimen-containing matrix is capable of being reproduced and which specimen-containing matrix is sectioned to a controlled thickness and stained and mounted and which specimen-containing matrix presents a uniform field constant from one area of the specimen-containing matrix to the next, and which exhibits spectra substantially the same as the characteristic spectra of the cells or tissue stained when subjected to light transmission analysis.

2. A standard specimen according to claim 1 wherein the biological material contains protein.

3. A standard specimen according to claim 1 wherein the biological material contains nucleic acid.

4. A standard specimen according to claim 1 wherein the biological material is selected from the group consisting of bovine liver acetone powder, nucleoprotamine or defatted horse muscle.

5. A standard specimen according to claim 1, wherein the plastic matrix is an epoxy.

6. A standard specimen according to claim 5, wherein the epoxy is glycol methacrylate epoxy.

7. A process for the preparation of a standard specimen for the quantitative evaluation of stain performance in staining processes which utilize dyes to stain cells or tissue and, which comprises incorporating a uniform amount of biological material extracted from cells or tissue into a plastic matrix, which specimen-containing matrix is capable of being reproduced and which specimen-containing matrix is sectioned to a controlled thickness and stained and mounted on a slide and which specimen-containing matrix presents a uniform field constant from one area of the specimen-containing matrix to the next when subjected to light transmission analysis.

8. A process according to in claim 7, wherein the biological material contains protein.

9. A process according to claim 7, wherein the biological material contains nucleic acid.

10. A process according to claim 7, wherein the biological material is selected from the group consisting of bovine liver acetone powder, nucleoprotamine or defatted horse muscle.

11. A process according to claim 7, wherein the plastic matrix is an epoxy.

12. A process according to in claim 11, wherein the epoxy is glycol methacrylate epoxy.

13. A method for evaluating stain or dye performance in staining processes which utilize dyes to stain cells or tissue, which comprises comparing, by means of quantitative analysis of parameters dependent on light transmission, a specimen treated with the stain or dye with a standard specimen, which standard specimen comprises a uniform amount of biological material extracted from cells or tissue which is incorporated into a plastic matrix, which specimen-containing matrix is capable of being reproduced and which specimen-containing matrix is sectioned to a controlled thickness ad stained and placed on a slide and which specimen-containing matrix presents a uniform field constant from one area of the specimen-containing matrix to the next when subjected to light transmission analysis.

14. A method for evaluating stain or dye performance according to claim 13, wherein the quantitative analysis is light transmission analysis which compares the respective light transmission of the specimen being evaluated with that of the standard specimen.

15. A method for evaluating a biological specimen comprising cells or tissue which method comprises comparing by means of quantitative analysis of parameters dependent on light transmission, the specimen to be evaluated with a standard specimen, which standard specimen comprises a uniform amount of biological material extracted from cells or tissue incorporated into a plastic matrix, which specimen-containing matrix is capable of being reproduced and which specimen-containing matrix is sectioned to a controlled thickness and stained and placed on a slide, and which specimen-containing matrix presents a uniform field constant from one area of the specimen-containing matrix to the next when subjected to light transmission analysis.

16. A method for evaluating a biological specimen according to claim 15, wherein the quantitative analysis is ploidy analysis.

17. A method for evaluating a biological specimen according to claim 15, wherein the quantitative analysis is integrated optical density analysis.

18. A method for evaluating a biological specimen according to claim 15, wherein the quantitative analysis is light scattering analysis.

19. A method for evaluating a biological specimen according to claim 15, wherein the quantitative analysis is the analysis of light polarization effects.

20. A method for evaluating a biological specimen according to claim 15, wherein the quantitative analysis is fluorescence analysis.

21. A method for evaluating stain or dye performance in staining processes which utilize dyes to stain cells or tissues, which comprises comparing a specimen treated with the stain or dye with a standard specimen, which comparison is carried out by means of quantitative analysis comparing the respective spectra when subjected to light transmission analysis of the specimen to be evaluated with the standard specimen, and which standard specimen comprises a uniform amount of nucleoprotamine which is incorporated into an epoxy matrix and mounted on a slide, which specimen-containing matrix is capable of being reproduced and which specimen-containing matrix is sectioned to a controlled thickness and stained and placed on a slide, and which specimen-containing matrix presents a uniform field constant from one area of the specimen-containing matrix to the next when subjected to light transmission analysis.

* * * * *